United States Patent [19]

Carter

[11] 4,200,834
[45] Apr. 29, 1980

[54] COMBINATION PROCESS SENSOR

[75] Inventor: William W. Carter, Livonia Center, N.Y.

[73] Assignee: Sybron Corporation, Rochester, N.Y.

[21] Appl. No.: 923,813

[22] Filed: Jul. 12, 1978

[51] Int. Cl.² ............................................ G01N 27/42
[52] U.S. Cl. .................................... 324/450; 324/54
[58] Field of Search ................ 324/54, 29, 30 R, 29.5, 324/30 B; 204/1 T

[56] References Cited

U.S. PATENT DOCUMENTS

| | | | |
|---|---|---|---|
| 3,831,085 | 8/1974 | Kratavil | 324/29 |
| 3,858,114 | 12/1974 | Voellmin | 324/54 |
| 3,863,146 | 1/1975 | Ehret | 324/29 |

Primary Examiner—M. Tokar
Attorney, Agent, or Firm—Theodore B. Roessel; J. Stephen Yeo

[57] ABSTRACT

A combination process sensor for use in electrically non-conducting lined steel vessels has a tantalum body containing a temperature sensitive element. One end of the body is positioned to be in contact with a product undergoing a process in the tank. Upon this end of the body there is fabricated an electrode, which allows the galvanic sensing of any faults which may occur in the glass lining.

5 Claims, 4 Drawing Figures

COMBINATION PROCESS SENSOR

RELATED PATENTS OR APPLICATIONS

My copending application, Ser. No. 923,814, filed July 12, 1978, discloses a method of fabricating electrodes which are well suited for practicing the present invention, and is hereby incorporated by reference.

BACKGROUND OF THE INVENTION

This invention relates to process sensors and is more particularly concerned with process sensors for use with electrically non-conducting lined steel vessels.

Glass lined steel vessels, for example, are widely used to process products in the chemical, food and beverage industries. The glass lining is relatively inert to acids while the steel vessel has the strength to withstand pressure and temperature extremes.

The lining is, under some circumstances, subject to corrosion or wear. This is undesirable as an interaction of the product and the steel could cause the steel to corrode, contaminating the product and affecting the integrity of the tank. Periodic visual inspection of the tank is recommended, but faults may be as small as pin holes and pass unnoticed. For this reason, electric fault finders have been developed which can continually monitor the tank for any fault which may be in the lining.

One type of fault finder uses the conductivity of the product to provide a reading. An electrode is immersed in the product and an electric potential is maintained between the electrode and the steel portion of the vessel. If there is a fault, the product will make contact with the steel and complete an electric circuit.

A second type of fault finder uses the electrolytic property of the product. A non-steel electrode is immersed in the product. If the product makes contact with the vessel steel a galvanic reaction occurs and an electric cell is then formed with the exposed steel as a second electrode. The voltage across the non-steel electrode and steel vessel body will give an indication of the condition of the lining. This invention is an improvement of this type of galvanic fault finder, while also providing means to measure temperature of the product.

PRIOR ART

Examples of galvanic fault finders are given U.S. Pat. Nos. 3,831,085, 3,858,114, and 3,863,146.

FIG. 1a illustrates a known galvanic fault finder electrode 10 and a separate known temperature sensor 22, both mounted in a steel vessel 13. FIG. 1b shows in detail an example of a non-steel galvanic fault finder having a non-ferrous electrode 10 mounted on a stem 11 of a flushing valve 12 arranged at the bottom of the steel vessel 13. As shown, the body 14 of the valve 12 is bolted to the vessel 13. The stem 11 of the valve is supported by a frame 15 which is electrically insulated from the valve body 14. The galvanic electrode 10 is attached to the head 16 of stem 11. All parts of the valve, which would be otherwise exposed to the product, are coated with electrically non-conducting material, such as glass. The active portion of the electrode 10 is preferably platinum because of galvanic considerations. In the particular example illustrated, a ⅜" threaded tantalum body 17 having a cap 18 was used. Only the cap 18 is exposed to the product and is at least partially plated or otherwise coated with platinum. The rest of the tantalum body is screwed into the valve head through a hole in the glass layer provided for that purpose. A seal 19 under the cap prevents the product for making contact with the steel valve head 16. An electrical contact 20 to the galvanic electrode 10 is made through the valve stem 11, which is electrically insulated from the body of the steel vessel 13. A contact 21 with the steel of the vessel 13 may be made at the valve housing 14.

FIG. 1c shows, in detail, a temperature sensor 22 known to the prior art. A hollow threaded tantalum body 23 contains a temperature sensitive element 24, such as a resistor having a temperature dependent resistance. One such resistor known to the prior art is a coil of platinum wire of about 100 ohms would upon a ceramic core. One end, 25, of the tantalum body 23 is in contact with the product so that the sensing 24 element is as in thermal communication with the product. Electric contact is made to the element 24 by means of leads 26, 27 and 28 running through the other end of the body.

The temperature sensor 22 is screwed into a hole provided in a glass-coated steel member 29 for support. The illustrated member is a baffle, constructed of one inch diameter steel pipe supported but electrically insulated from the tank at a stuffing head.

Enough of the sensor is exposed to allow a sealing gasket 30 to be placed over the body 23 so as to surround it. Gasket 30 is held in place by a nut 31 threaded on the exposed portion of the body. It is important to note, to appreciate the invention, that electrical contact is made to the temperature element 24 only by leads and that the tantalum body of the sensor is not used as an electric conductor.

Returning to FIG. 1a, it is seen that two separate sensors have been required to measure temperature and to provide a galvanic fault finder. Furthermore, there may not be enough room to mount a separate fault sensor and temperature sensor on the same member.

DETAILED DESCRIPTION OF THE INVENTION

While the invention will be described in connection with a preferred embodiment of a combination sensor, it will be understood that it is not intended to limit the invention to that embodiment. On the contrary, it is intended to cover all alternatives, modifications and equivalents as may be included within the spirit and scope of the invention as defined by the appended claims.

Figure 1:
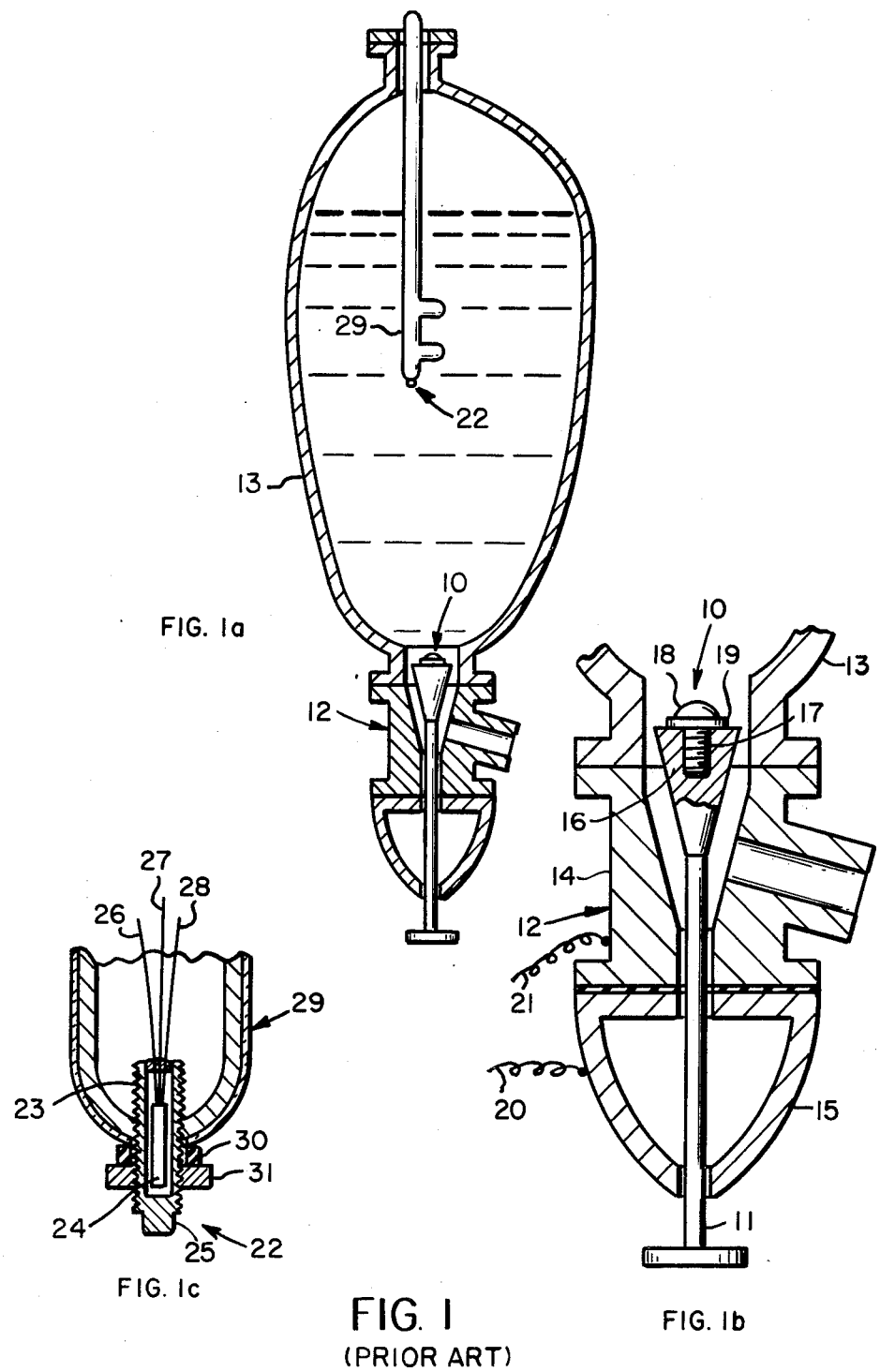
FIG. 1a shows a fault finder sensor and a temperature sensor, both of which are known to the prior art, mounted in a vessel.
FIG. 1b shows in more detail the prior art fault finding sensor.
FIG. 1c shows in further detail the prior art temperature sensor.
Figure 2:
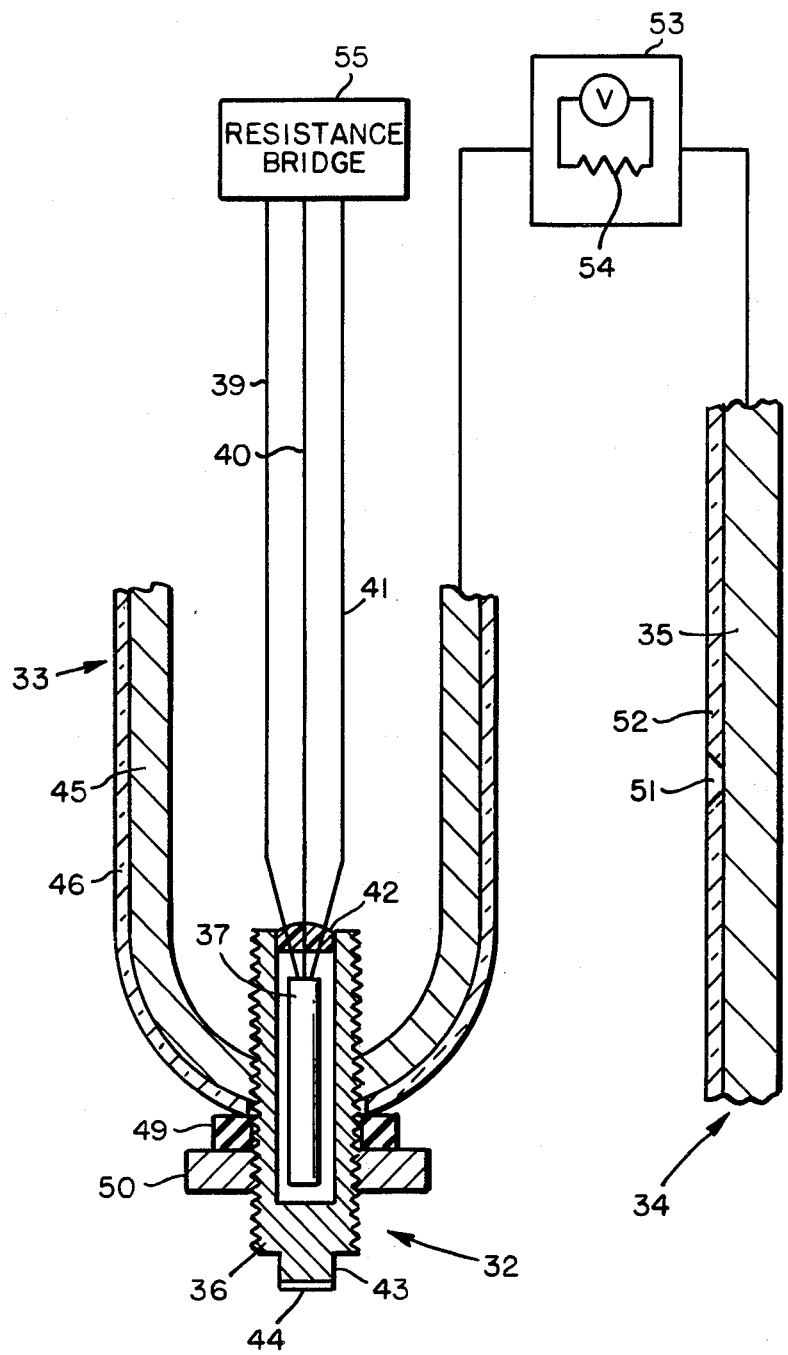
FIG. 2, illustrates, in cross section, a combination sensor built in accordance with the present invention.

Referring to FIG. 2, there is shown, in cross section, a sensor 32, built in accordance with the present invention, secured to a hollow conductive structure 33 which may be steel, coated with glass 46 or other electrically non-conducting material. The sensor 32 is positioned so that one end 43 is in contact with a product contained within a glass-lined steel vessel 34. The structure 33 supporting the sensor 32 is electrically insulated from the steel body 35 of the vessel. The structure 33 illustrated by the drawing may be a baffle, or another member of the vessel electrically insulated from the steel vessel and tapped to receive the sensor 32. A specific example of an alternative structure is the head of a flush valve, such as discussed in the background of the invention.

The body 36 of the sensor 32 is preferably constructed of tantalum and is fabricated from threaded cylindrical stock. The body 36 includes a cavity 37 containing a temperature sensor element 38, such as a resistor found by platinum wire coiled about a ceramic core. The element 38 is not in electrical contact with the body 36, but rather, leads 39, 40, 41 are provided to make all necessary electrical connections to the elements.

A clot of potting compound 42 may be used to support the leads 39, 40, 41 and to seal the cavity 37 of the sensor. The leads 36, 37 and 38 are fed through the supporting structure 33 to a point external to the vessel.

The end 43 of the body in contact with the product is solid, that is to say there is no holes through the surface of that end of the body which are in communication with the interior of the body. According to my invention, the solid end of the body is at least partially covered with platinum 44 which may be plated or deposited on layers or defused into the tantalum surface. The preferred method is to platinize the end 43 of the body by firing a platinum layer in accordance with my afore cited copending application, Ser. No. 923,814, filed Jul. 12, 1978. The method taught provides a hard and long wearing platinized surface well suited for the sensor.

The sensor body 36 is screwed into the steel part 45 of glass-lined supporting structure 33 through a hole in the glass layer 46 provided for that purpose. A sealing gasket 49 is placed around the sensor 32 and compressed by nut 50 threaded upon the exposed end of the sensor body. Alternatively, the body 36 may include a cap, in which case a nut may not be required.

The temperature element 38 will be in thermal communication with the product and the leads running through the structure will allow external monitoring of the temperature, by use of a first detecting means 55, such as a resistance bridge.

The platinum covered end 44 of the sensor is arranged to be normally in direct contact with the product. Structure 33 is an electrical contact with the sensor body 36 and thereby with the platinum covered end 44. Should a fault 51 occur in the glass lining 52 of the vessel 34, the product will make contact with the steel portion 35 of the vessel. Most products, the exception being highly alkaline liquids and the like, will function as electrolytes, so that a galvanic reaction will then occur, with the platinized area 44 and the exposed steel 35 being electrodes. Recalling that the platinized area 44 is in electrical communication with structure 33, the voltage resulting from the galvanic reaction will also appear between the steel 45 of the supporting structure 33 and the steel 35 of the glass-lined vessel 34. The galvanic reaction may be observed by a second detecting means 55. For example, the galvanic voltage will cause current flow through a resistor 54 connected between the supporting structure and the steel of the vessel. This current can be monitored to provide indication of any fault which may occur in the glass-lined tank.

The sensor is therefore in fact a combination sensor which will both measure product temperature and function as a fault sensor. Separate electrical circuits are maintained, as leads maintain electrical contact to the temperature element 38, whereas, the tantalum body of the sensor 32 in series with the steel 48 of structure 33, provides electrical access to the platinum electrode 44.

Thus it is apparent that there has been provided, in accordance with the invention, a combination sensor that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A sensor for a steel vessel having an electrically non-conducting liner, for measuring temperature of a product contained in the vessel and monitoring for faults occurring in the non-conductive lining of the vessel, said sensor adapted to be supported in the vessel by a conductive structure electrically insulated from the vessel, said sensor comprising:
   a tantalum body having a cavity extending within to a first end of the body;
   temperature sensitive means contained in the cavity and electrically insulated from the body;
   electrical leads extending from said temperature sensitive means from said cavity; and
   said body having a second end for contacting the product during use, said second end being at least partially covered with platinum, wherein electrical access is provided to the second end through said conductive structure.

2. A sensor for glass-lined steel vessel for measuring temperature of a product contained in the vessel and monitor for faults occurring in the glass lining of the vessel, said sensor adapted for being supported in the vessel by a tapped glass coated steel member electrically insulated from the vessel, said sensor comprising:
   a threaded cylindrical tantalum body having a cavity, extending within to a first end of the body;
   temperature sensitive means contained in the cavity and electrically insulated from the body;
   electrically leads extending from said temperature sensitive means from said cavity; and said body having a second end for contacting the product during use, said second end being at least partially platinum.

3. Apparatus according to claim 1 or 2 wherein said non-conducting lining in glass, and said metallic member is coated with glass.

4. Apparatus according to claim 3, wherein said tantalum body has a cylindrical portion with an external thread, and said cylindrical portion is mounted in a tapped hole in said metallic member.

5. Apparatus according to claim 4 wherein said metallic member comprises a baffle or a flush valve.